(12) United States Patent
Tanaka et al.

(10) Patent No.: US 7,531,520 B2
(45) Date of Patent: May 12, 2009

(54) DRUG AND FOOD OR DRINK FOR IMPROVING PANCREATIC FUNCTIONS

(75) Inventors: Miyuki Tanaka, Zama (JP); Eriko Misawa, Zama (JP); Noriko Habara, Zama (JP); Muneo Yamada, Zama (JP)

(73) Assignee: Morinaga Milk Industry Co., Ltd., Minato-ku, Tokyo (JP)

( * ) Notice: Subject to any disclaimer, the term of this patent is extended or adjusted under 35 U.S.C. 154(b) by 84 days.

(21) Appl. No.: 11/576,676

(22) PCT Filed: Feb. 28, 2006

(86) PCT No.: PCT/JP2006/303708

§ 371 (c)(1), (2), (4) Date: Apr. 4, 2007

(87) PCT Pub. No.: WO2006/123464

PCT Pub. Date: Nov. 23, 2006

(65) Prior Publication Data

US 2008/0125379 A1   May 29, 2008

(30) Foreign Application Priority Data

May 17, 2005   (JP) .............................. 2005-144386

(51) Int. Cl.
A01N 45/00 (2006.01)
A61K 9/00 (2006.01)
A61K 36/00 (2006.01)

(52) U.S. Cl. .......................... 514/26; 424/725; 424/400

(58) Field of Classification Search ....................... None
See application file for complete search history.

(56) References Cited

U.S. PATENT DOCUMENTS 4,598,069 A   7/1986   Hikino et al.

FOREIGN PATENT DOCUMENTS

| EP | 0 861 595 | 9/1998 |
|----|-----------|--------|
| EP | 1 125 584 | 8/2001 |
| JP | 60-214741 | 10/1985 |
| JP | 10-330266 | 12/1998 |
| JP | 2003-113111 | 4/2003 |
| JP | 2003-286185 | 10/2003 |
| WO | WO 97/17086 | 5/1997 |
| WO | WO 99/19505 | 4/1999 |
| WO | WO 03/059360 | 7/2003 |
| WO | WO 2005/095436 | 10/2005 |

OTHER PUBLICATIONS

Abou Zeid, "Chemical and Biological Study of the Leaves of Some *Musa* Species," *Egypt. J. Pharm. Sci*, vol. 39, Nos. 4-6, pp. 379-398, 1998.
Yeh, et al. "Systematic Review of Herbs and Dietary Supplements for Glycemic Control in Diabetes," *Diabetes Care*, vol. 26, No. 4, pp. 1277-1294, Apr. 2003.
International Search Report dated Apr. 24, 2006.
Bunyapraphatsara, et al., "Antidiabetic Activity of *Aloa vera L.* juice II. Clinical Trial in Diabetes Mellitus Patients in Combination with Glibenclamide," *Phytomedicine*, vol. 3, No. 3, pp. 245-248, 1996.
Beppu, et al. "Hypoglycaemic and Antidiabetic Effects in Mice of *Aloe arborescens* Millar Var. *natalensis* Berger," *Phytotherapy Research*, vol. 7, pp. S37-S42, 1993.
Nes, W. David, "Sterol Methyl Transferase: Enzymology and Inhibition," *Biochimica et Biophysica Acta*, 1529, pp. 63-88, 2000.
Okyar, et al. "Effect of *Aloe vera* Leaves on Blood Glucose Level in Type I and Type II Diabetic Rat Models," *Phytotherapy Research*, vol. 15, pp. 157-161, 2001.
Panosyan, et al. "Sterols and Sterol Glycosides of *Bryonia alba*," *Khimiya Prirodynykh Soedinenii*, vol. 3, pp. 353-360, 1977.
Beppu, et al. "Radical-Scavenging Effects of *Aloe arborescens* Miller on Prevention of Pancreatic Islet B-Cell Destruction in Rats," *Journal of Ethnopharmacology*, vol. 89, Issue 1, pp. 37-45, Nov. 2003.

*Primary Examiner*—Christopher R Tate
*Assistant Examiner*—Randall Winston
(74) *Attorney, Agent, or Firm*—Knobbe, Martens, Olson & Bear, LLP

(57) ABSTRACT

3-O-β-D-Glucopyranosyl-4-methyl-ergost-7-en-3-ol or a composition containing 0.001 to 10% by dry mass of the aforementioned compound, which is an extract of a plant of the family Liliaceae or a fraction thereof containing the compound, is used as an active ingredient of a drug for improving pancreatic functions.

3 Claims, 4 Drawing Sheets

US 7,531,520 B2

DRUG AND FOOD OR DRINK FOR IMPROVING PANCREATIC FUNCTIONS

RELATED APPLICATIONS

This application is the U.S. National Phase under 35 U.S.C. § 371 of International Application PCT/JP2006/303708, filed Feb. 28, 2006, which was published in a non-English language, which claims priority to Japanese Patent Application No. 2005-144386, filed May 17, 2005.

TECHNICAL FIELD

The present invention relates to a drug and food or drink for improving pancreatic functions, which contains 3-O-β-D-glucopyranosyl-4-methyl-ergost-7-en-3-ol.

BACKGROUND ART

4-Methyl-ergost-7-en-3-ol is known to be a substance that exists in plants (Non-patent document 1). As for prior arts of this compound, however, there is only a reference concerning the biosynthetic system of lophenol (one of the stereoisomers of 4-methyl-cholest-7-en-3-ol) having a structure similar to that of the aforementioned compound (Non-patent document 2), and the use of these compounds having the lophenol skeleton including 4-methyl-ergost-7-en-3-ol is not known at all.

The genus *Aloe* in the family Liliaceae is a group of plants including *Aloe vera* (*Aloe barbadensis* Miller), *Aloe arborescens* (*Aloe arborescens* Miller var. *natalensis* Berger) and so forth, and they are empirically known to have various efficacies. The prior arts regarding the use of plants of the genus *Aloe* include immunomodulating polysaccharides (Patent document 1), immunosuppression improving agents containing a butanol fraction of an aloe extract or aloin (Patent document 2), HSP60 family protein synthesis suppressing agents containing aloin derivatives (Patent documents 3 to 5), proteins having lectin activity derived from aloe leaf-skin (Patent document 6), use for improvement of blood glucose levels (Non-patent document 3 to 7, Patent document 7 to 10) and so forth.

The pancreas is an organ constituted by endocrine gland tissues called the pancreas islets (Langerhans islets) and exocrine gland tissues secreting digestive enzymes. The β cells, α cells, δ cells, pancreatic polypeptide cells, and so forth exist in the Langerhans islets, and they greatly affect the control of blood glucose and metabolism. Among these, the β cells play a particularly important role as cells producing insulin.

Diabetes mellitus is a highly frequently observed metabolic disorder recognized in 10% of Japanese adults. According to the epidemiology of the β cell dysfunction of the pancreas, which is considered one of the causes of diabetes mellitus, while the β cell dysfunction is of course observed in individuals with borderline type hyperglycemia, individuals exhibiting normal glucose tolerance also include individuals exhibiting clearly reduced β cell functions at a rate of 30%. Moreover, it is said that adults who lead average social life in present-day Japan highly frequently causes insulin resistance more or less, and it is considered that, as for persons suffering from insulin resistance, in those who do not suffer from β cell dysfunction, the blood glucose level does not increase, and in those who suffer from β cell dysfunction, the blood glucose level increases from a level corresponding to normal glucose tolerance to a level corresponding to borderline type hyperglycemia (Non-patent document 8).

At present, although therapies for promoting spontaneous recovery of the pancreatic functions based on removal of causative pathological conditions or factors are used for pancreatic function disorder, any therapeutic method or agent for positively restoring pancreatic functions once degraded has not been used so far, and agents for protecting pancreatic cells or agents for improving damaged pancreatic cells are desired in the clinical field.

The pancreatic function disorder means a pathological condition that the endocrine or exocrine gland functions of the pancreas are lowered or abnormally enhanced.

As the prior art of agents for curing pancreatic function disorder, those containing neurotrophic factors such as BDNF as an active ingredient (Patent document 11), those containing glycerol derivatives as an active ingredient (Patent document 12), pancreatic function improving agents containing betacellulin proteins or muteins thereof (Patent document 13), and so forth. It has been so far considered that BDNF is released from the central end of small DRG neuron with other transmitters at the time of inflammation or nerve damage, and involved in promotion of pain signal transduction via tyrosine phosphorylation of the NMDA receptor on the dorsal horn cells (Non-patent document 9), and thus it is considered to be restricted for actual use.

Further, the glycerol derivatives disclosed in Patent document 12 are the compounds described in Patent document 14, and are agents having antiplatelet-activating factor (PAF) activity for therapeutic and prophylactic treatment of DIC, shock, allergy, acute pancreatitis, brain twitch at the time of subarachnoid haemorrhage, and so forth, and they are also found to have an organopathy preventing, curing and improving effect for preventing, curing and improving organopathy caused in processes of preservation of organ in ischemic condition, blood flow obstruction caused by post-graft blood reperfusion or surgery, and so forth. However, it is hard to say that these agents are suitable for chronic pancreatic diseases without these symptoms.

Moreover, the pancreatic function improving agents containing betacellulin proteins or muteins thereof disclosed in Patent document 13 also have an action of acting on undifferentiated pancreatic stem cells and thereby promoting differentiation of them into the pancreatic β cells producing insulin, and an action of inducing differentiation of undifferentiated stem cells into other cells of the pancreas such as F cells producing pancreatic polypeptides, and the effect cannot be expected under a condition that immature cells are depleted. In addition, although mRNAs of these proteins are detected in various organs other than the brain, for example, liver, kidney, pancreas, etc., the details of the functions thereof are not clarified almost at all, and therefore it cannot be said that they can be immediately used for clinical cases.

Furthermore, it has been disclosed in patent document 15 that compounds having a lanostane skeleton or 3,4-secolanostane skeleton have an insulin action enhancing activity. The effect of these compounds is to enhance the insulin action in regulation of adipocyte differentiation, and the effect thereof on pancreatic diseases remains unknown.

As for a glycoside having a plant-derived lophenol skeleton, it has been reported that 3-O-β-D-glucopyranosyl-4-methyl-stigmast-7-en-3-ol is contained in Bryony (*Bryonia alba*), a plant of the family Cucurbitaceae (Non-patent document 10). However, this is not a plant that has been generally eaten, and no total synthesis thereof has been reported.

[Patent document 1] International Patent Application Unexamined Publication in Japanese (Kohyo) No. 2001-520019

[Patent document 2] Japanese Patent Laid-open (Kokai) No. 08-208495

[Patent document 3] Japanese Patent Laid-open No. 10-120576
[Patent document 4] Japanese Patent Laid-open No. 10-045604
[Patent document 5] Japanese Patent Laid-open No. 10-036271
[Patent document 6] Japanese Patent Laid-open No. 09-059298
[Patent document 7] Japanese Patent Laid-open No. 60-214741
[Patent document 8] Japanese Patent Laid-open No. 2003-286185
[Patent document 9] U.S. Pat. No. 4,598,069
[Patent document 10] U.S. Patent Application Publication No. 2003/0207818
[Patent document 11] International Publication No. WO 00/62796
[Patent document 12] Japanese Patent Laid-open No. 07-285866
[Patent document 13] Japanese Patent Laid-open No. 09-188630
[Patent document 14] Japanese Patent Laid-open No. 02-131467
[Patent document 15] Japanese Patent Laid-open No. 10-330266
[Non-patent document 1] Chem. Pharm. Bull., pp. 624-626, 1993
[Non-patent document 2] Biochimica Biophysica Acta, pp. 63-88, 2000
[Non-patent document 3] Phytomedicine, Vol. 3, pp. 245-248, 1996
[Non-patent document 4] Phytotherapy Research, Vol. 15, pp. 157-161, 2001
[Non-patent document 5] Phytotherapy Research, Vol. 7, pp. 37-42, 1993
[Non-patent document 6] Nippon Rinsho, No. 748, Vol. 1, pp. 615-617, 1999
[Non-patent document 7] Nippon Rinsho, No. 808, Vol. 2, pp. 405-409, 2002
[Non-patent document 8] "Insulin Resistance," Diabetes Mellitus current library, Bunkodo, Apr. 17, 2004
[Non-patent document 9] Brain Res Rev, Vol. 40, pp. 240-249, 2002
[Non-patent document 10] Khimiya Prirodnykh Soedinenii, Vol. 3, USSR, 1977

DISCLOSURE OF THE INVENTION

An object of the present invention is to provide a drug and food or drink suitable for improving pancreatic functions, which does not contain unfavorable ingredients for a drug and food or drink, from a raw material that can be taken safely from experiential viewpoint for food and is readily obtained.

The inventors of the present invention assiduously studied in order to achieve the foregoing objects. As a result, they found that 3-O-β-D-glucopyranosyl-4-methyl-ergost-7-en-3-ol, a novel glycoside extracted and purified from mesophyll (clear gel portion) of *Aloe vera* (*Aloe barbadensis* Miller), could be safely ingested and had an activity for protecting pancreatic endocrine gland cells or improving functions of the pancreatic endocrine gland cells. The present invention was accomplished on the basis of the above findings.

That is, the present invention provides a drug for improving pancreatic functions, which contains a compound represented by the following chemical formula (1) as an active ingredient. According to a preferred embodiment of the drug of the present invention, the improvement of pancreatic functions is to protect pancreatic endocrine gland cells or to improve pancreatic endocrine gland cell functions:

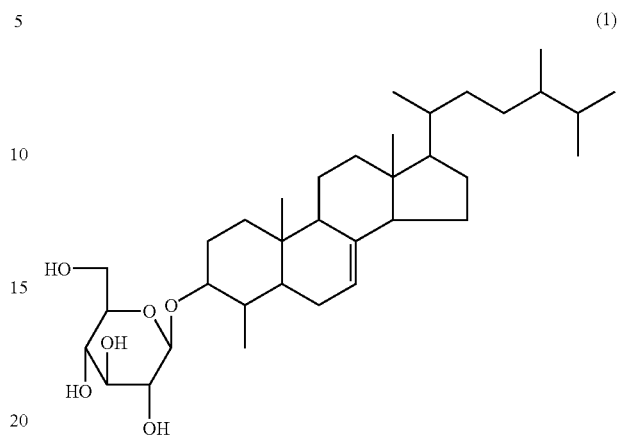

(1)

According to a preferred embodiment, the drug of the present invention contains 0.001 to 10% by dry mass of the aforementioned compound.

The present invention also provides a drug for improving pancreatic functions, which comprises an extract of a plant of the family Liliaceae or a fraction thereof containing 0.001 to 10% by dry mass of a compound represented by the aforementioned chemical formula (1) as an active ingredient. According to a preferred embodiment of the drug of the present invention, the improvement of pancreatic functions is to protect pancreatic endocrine gland cells or to improve pancreatic endocrine gland cell functions.

The present invention further provides a food or drink for improving pancreatic functions, which comprises a compound represented by the aforementioned chemical formula (1). According to a preferred embodiment of the food or drink of the present invention, the improvement of pancreatic functions is to protect pancreatic endocrine gland cells or to improve pancreatic endocrine gland cell functions.

Further, according to a preferred embodiment, the food or drink of the present invention contains 0.0001 to 1% by dry mass of the aforementioned compound.

Further, the present invention provides a food or drink for improving pancreatic functions, which comprises an extract of a plant of the family Liliaceae or a fraction thereof containing 0.0001 to 1% by dry mass of a compound represented by the aforementioned chemical formula (1). According to a preferred embodiment of the food or drink of the present invention, the improvement of pancreatic functions is to protect pancreatic endocrine gland cells or to improve pancreatic endocrine gland cell functions. According to a preferred embodiment, the food or drink of the present invention is attached with an indication that the food or drink is used for improving pancreatic functions.

The present invention further provides use of a compound represented by the aforementioned chemical formula (1) or a composition containing the same in the production of a drug for improving pancreatic functions. According to a preferred embodiment of the use of the present invention, the improvement of pancreatic functions is to protect pancreatic endocrine gland cells or to improve pancreatic endocrine gland cell functions. Further, according to a preferred embodiment of the use of the present invention, the aforementioned composition comprises an extract of a plant of the family Liliaceae or a fraction thereof which contains 0.001% by dry mass or more of the aforementioned compound.

The present invention further provides a method for protecting pancreatic endocrine gland cells or improving functions of the cells, which comprises administering a compound represented by the aforementioned chemical formula (1) or a composition containing the same to a subject whose pancreatic endocrine gland cells are to be protected or functions of the cells are to be improved. According to a preferred embodiment of the method of the present invention, the improvement of pancreatic functions is to protect pancreatic endocrine gland cells or to improve pancreatic endocrine gland cell functions. Further, according to a preferred embodiment of the method of the present invention, the aforementioned composition comprises an extract of a plant of the family Liliaceae or a fraction thereof which contains 0.001% by dry mass or more of the aforementioned compound.

BEST MODE FOR CARRYING OUT THE INVENTION

Figure 1:
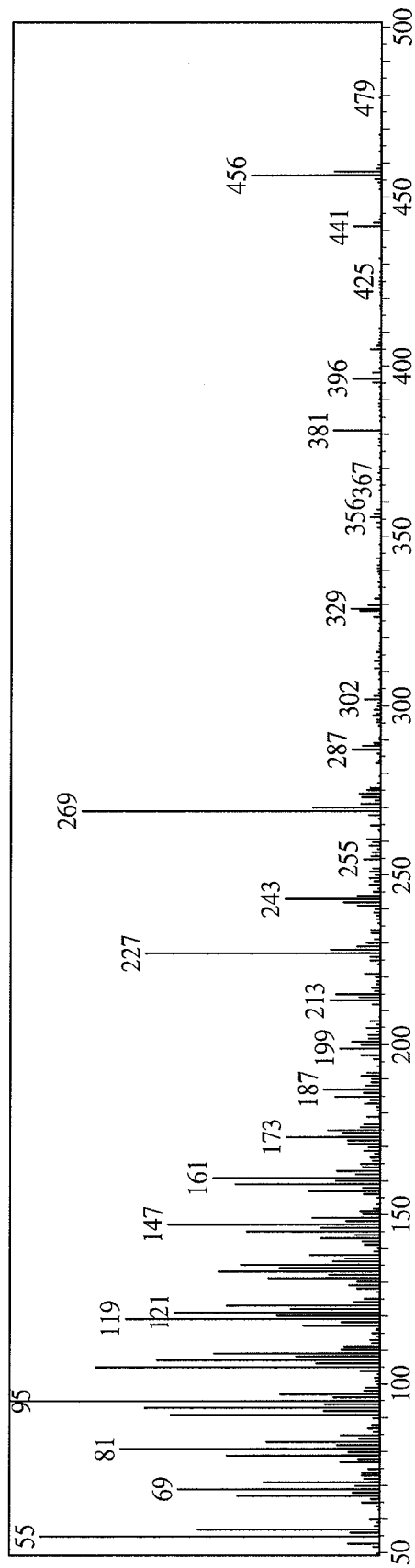
FIG. 1 shows a GC-MS spectrum of the acetylated aglycon moiety of the glycoside of the present invention (photo to replace drawing: a half-tone image shown on a display).

Hereafter, preferred embodiments of the present invention will be explained in detail. However, the present invention is not limited to the following preferred embodiments and can be freely modified within the scope of the present invention.

The compound used as an active ingredient of the drug and food or drink of the present invention (hereinafter also referred to as "the compound of the present invention") is a compound having a structure represented by the aforementioned chemical formula (1), that is, 3-O-β-D-glucopyranosyl-4-methyl-ergost-7-en-3-ol. That is, the compound of the present invention has a structure formed by dehydration condensation of the hydroxyl group at the 3-position of 4-methyl-ergost-7-en-3-ol and the hydroxyl group at the 1-position of D-glucose.

Furthermore, the composition used as an active ingredient of the drug and food or drink of the present invention (hereinafter also referred to as "the composition of the present invention") is an extract of a plant of the family Liliaceae or a fraction thereof containing 0.001% by dry mass or more, preferably 0.01% by dry mass or more, more preferably 0.1% by dry mass or more, of the aforementioned compound of the present invention when used as an active ingredient of a drug, or containing 0.0001% by dry mass or more, preferably 0.001% by dry mass or more, more preferably 0.1% by dry mass or more, of the aforementioned compound of the present invention when used as an active ingredient of a food or drink. The upper limit of the content of the compound of the present invention contained in the composition of the present invention is not particularly limited, and it may be, for example, 50, 70 or 90% by mass.

The compound of the present invention or a composition containing the same can be produced by, for example, extracting a fraction containing the compound of the present invention from a plant belonging to the family Liliaceae and containing the compound of the present invention, a part thereof, or a disruption product thereof by using an organic solvent or hot water and concentrating the fraction.

Examples of the aforementioned plant belonging to the family Liliaceae include plants belonging to the genus *Aloe* or *Allium*. Examples of the plants of the genus *Aloe* include *Aloe barbadensis* Miller, *Aloe ferox* Miller, *Aloe africana* Miller, *Aloe arborescen* Miller var. *natalensis* Berger, *Aloe spicata* Baker and so forth. In the production of the compound of the present invention or a composition containing the same, although the whole of the aforementioned plant may be used, it is preferable to use mesophyll (clear gel portion) thereof. Such a plant or a part thereof is disrupted preferably by using a homogenizer or the like and thereby liquefied, and the compound of the present invention or a composition containing the same is extracted from the disruption product by using an organic solvent or hot water. Examples of the organic solvent include alcohols such as methanol, ethanol and butanol and so forth; esters such as methyl acetate, ethyl acetate, propyl acetate and butyl acetate and so forth; ketones such as acetone and methyl isobutyl ketone and so forth; ethers such as diethyl ether and petroleum ether and so forth; hydrocarbons such as hexane, cyclohexane, toluene and benzene and so forth; halogenated hydrocarbons such as carbon tetrachloride, dichloromethane and chloroform and so forth; heterocyclic compounds such as pyridine and so forth; glycols such as ethylene glycol and so forth; polyhydric alcohols such as polyethylene glycol and so forth; nitrile solvents such as acetonitrile and so forth, mixtures of these solvents and so forth. Furthermore, these solvents may be anhydrous or hydrous. Among these solvents, ethyl acetate/butanol mixture (3:1) and chloroform/methanol mixture (2:1) are particularly preferred.

As the extraction method, a method used for usual extraction of a plant component can be used. Usually used is, for example, a method of refluxing 1 to 300 parts by mass of an organic solvent with 1 part by mass of fresh plant or dried plant with heating at a temperature at or below the boiling point of the solvent and stirring or shaking, or a method of performing extraction by ultrasonication at room temperature. By isolating insoluble matters from the extraction liquor using a suitable method such as filtration or centrifugation, a crude extract can be obtained.

The crude extract can be purified by various types of chromatography such as normal or reverse phase silica gel column chromatography. When a gradient of chloroform/methanol mixture is used in normal phase silica gel column chromatography as an elution solvent, the compound of the present invention is eluted with a mixing ratio of chloroform: methanol=about 5:1. Furthermore, when a gradient of methanol/water mixture is used in reverse phase silica gel column chromatography as an elution solvent, the compound of the present invention is eluted with methanol of a concentration of about 95%.

The obtained fraction can be further purified by HPLC or the like.

Whether the compound or composition containing the same obtained as described above actually contains the compound of the present invention can be confirmed by, for example, the methods shown in the examples described later. Whether the compound is a glycoside bound with glucose at the aglycon moiety, or whether the aglycon moiety is 4-methyl-ergost-7-en-3-ol can be confirmed by, for example, $^{13}$C-NMR or the like.

The inventors of the present invention previously also found that 3-O-β-D-glucopyranosyl-4-methyl-ergost-7-en-3-ol also had a blood glucose level improving action, and 3-O-β-D-glucopyranosyl-4-methyl-ergost-7-en-3-ol of *Aloe vera* was purified in Preparation Example 1 mentioned later by using evaluation of the blood glucose level improving action shown in Reference Example 1 as an index. However, it can also be purified by using the pancreatic function improving action, in particular, the pancreatic endocrine gland cell protecting action or pancreatic endocrine gland cell function improving action as an index.

The compound of the present invention can also be produced by condensing D-glucose and 4-methyl-ergost-7-en-3-ol. 4-Methyl-ergost-7-en-3-ol can be obtained by extracting from a plant and purifying it. D-Glucose and 4-methyl-ergost-7-en-3-ol can be condensed by, for example, a combination of the methods described in Jikken Kagaku Koza (Lecture of Experimental Chemistry), 4th edition, vol. 26, 1992 (described in p. 272, p. 297 and p. 342). That is, D-glucose is completely acetylated, and then the anomeric position is converted to α-bromide. Then, 4-methyl-ergost-7-en-3-ol is reacted with α-bromide in diethyl ether to attain β-glycosylation, and thereafter the acetyl group is hydrolyzed in a sodium methoxide/methanol mixture to obtain the objective compound.

The compound of the present invention has a pancreatic function improving action, in particular, pancreatic endocrine gland cell protecting action or pancreatic endocrine gland cell function improving action. It can be used as an active ingredient of a drug and food or drink for improving pancreatic functions, in particular, protecting pancreatic endocrine gland cells or improving pancreatic endocrine gland cell functions. In the present invention, protection of pancreatic endocrine gland cells means to protect the pancreatic endocrine gland cells from denaturation due to various causes, or to prevent decrease of the insulin production ability of the pancreatic endocrine gland cells. Further, improvement of pancreatic endocrine gland cell functions means to enhance the insulin production ability of the pancreatic endocrine gland cells of which insulin production ability decreases. Denaturation of pancreatic endocrine gland cells, or protection of pancreatic endocrine gland cells or improvement of pancreatic endocrine gland cell functions can be evaluated by microscopic observation of a pancreatic tissue section of an animal or measurement of serum insulin level.

By the aforementioned actions, the compound of the present invention can prevent decrease of the insulin production ability of pancreatic endocrine gland cells, or enhance the insulin production ability of pancreatic endocrine gland cells of which insulin production ability decreases.

As for the db/db mice used in the examples mentioned later, it is known that affection of the pancreas is observed in them with aging in terms of week (Science, 153, 1127-1128, 1966). Although it has been reported that if N-acetyl-L-cysteine, vitamin C and vitamin E as compounds having an anti-oxidation action are administered to these mice in combination, decrease of the β cell number in the pancreas can be partially prevented (Diabetes, 48, 2398-2406, 1999), even the dose of only N-acetyl-L-cysteine is 100 g/60 kg, and it is expected that administration in extremely large doses is required. In contrast, according to the present invention, it can be expected that the pancreatic endocrine gland cell protecting action or the pancreatic endocrine gland cell function improving action can be attained with a small dose.

The drug of the present invention can be used as an active ingredient of agents for a prophylactic treatment or therapeutic treatment of diseases caused by hypofunction of pancreatic endocrine gland cells, for example, pancreatic function disorder in acute pancreatitis, chronic pancreatitis, type I diabetes mellitus, and type II diabetes mellitus, pancreatic hypofunction associating with senile decrease of insulin secretion, and so forth. Moreover, since the compound of the present invention exhibits low toxicity, it can also be used together with an antitumor agent in a treatment of pancreatic cancer. Preferably, an agent used for improving hyperglycemia among the diseases accompanying decrease in insulin production ability is not encompassed within the scope of the drug of the present invention.

Furthermore, because leaf-skin of *Aloe vera* contains barbaloin and aloe-emodin having a laxative action, it is conventionally considered to be unfavorable as a drug and food or drink for which laxative action is not expected. On the other hand, the composition of the present invention according to a preferred embodiment can be obtained by extraction and fractionation from mesophyll (clear gel portion) of *Aloe vera*, which can be safely ingested from experiential viewpoint for food, and therefore it does not contain barbaloin or aloe-emodin, but contains an effective amount of the compound of the present invention. Therefore, the composition of the present invention is also preferred as an active ingredient of a drug for protection of pancreatic endocrine gland cells or improvement of functions of pancreatic endocrine gland cells.

The compound or composition of the present invention per se can be utilized as an active ingredient of the drug and food or drink of the present invention. Furthermore, the composition of the present invention may be a solution and can also be stored and used as powder after it is lyophilized or spray-dried in a conventional manner.

As the drug of the present invention, the compound or the composition of the present invention or those combined with a pharmaceutically acceptable carrier can be orally or parenterally administered to a mammal including human. In the drug of the present invention, the compound of the present invention may be a pharmaceutically acceptable salt. Examples of the pharmaceutically acceptable salt include both metal salts (inorganic salts) and organic salts including, for example, those listed in "Remington's Pharmaceutical Sciences", 17th edition, p. 1418, 1985. Specific examples thereof include, but not limited to, inorganic acid salts such as hydrochloride, sulfate, phosphate, diphosphate, and hydrobromate, and organic acid salts such as malate, maleate, fumarate, tartarate, succinate, citrate, acetate, lactate, methanesulfonate, p-toluenesulfonate, pamoate, salicylate and stearate. Furthermore, the salt may be a salt with a metal such as sodium, potassium, calcium, magnesium, aluminum and so forth, or a salt with an amino acid such as lysine and so forth. Furthermore, solvates such as hydrates and so forth of the aforementioned compound or pharmaceutically acceptable salts thereof also fall within the scope of the present invention.

Dosage form of the drug of the present invention is not particularly limited and can be suitably selected depending on the therapeutic purpose. Specific examples thereof include tablet, pill, powder, solution, suspension, emulsion, granules, capsule, syrup, suppository, injection, ointment, patch, eye drop, nasal drop and so forth. For the preparation, additives generally used in usual therapeutic or preventive drugs for diseases of internal organs such as pancreas as pharmaceutical carriers such as excipients, binders, disintegrating agents, lubricants, stabilizers, flavoring agents, diluents, surfactants and solvents for injection and so forth can be used. Furthermore, so long as the effect of the present invention is not degraded, the compound or composition of the present invention can be used in combination with other drugs having pancreatic disease improving or preventing effect.

Although the amount of the compound or the composition of the present invention contained in the drug of the present invention is not particularly limited and can be suitably selected, the amount may be, for example, 0.001 to 10% by mass, preferably 0.01 to 1% by mass, particularly preferably 0.05 to 1% by mass, in terms of the amount of the compound of the present invention.

Furthermore, with the drug of the present invention, various diseases, complications and so forth resulted from hypofunction of pancreatic endocrine gland cells can be prevented, and risks of these diseases, complications and so forth can be reduced.

Examples of such various diseases and complications resulted from hypofunction of pancreatic endocrine gland cells include nerve disorder, nephropathy, retinopathy, cataract, macrovascular disease, diabetes mellitus and so forth.

The administration time of the agent or drug of the present invention is not particularly limited and can be suitably selected according to the method for treating an objective disease. Furthermore, the administration route is preferably determined depending on the dosage form, age, sex and other conditions of patients, severity of symptoms of patients and so forth.

The dose of the active ingredient in the drug of the present invention is suitably selected depending on the dosing regimen, age and sex of patients, severity of disease, other conditions of patients and so forth. The amount of the compound of the present invention as an active ingredient is usually selected from the range of, preferably 0.01 to 10 mg/kg/day, more preferably 0.1 to 1 mg/kg/day, as a tentative dose. Furthermore, when the composition of the present invention is used, the dry weight of the composition is selected from the range of, preferably 0.1 to 1000 mg/kg/day, more preferably 1 to 100 mg/kg/day, as a tentative amount. In any case, the dose can be administered once daily or several times as divided portions.

The compound or the composition of the present invention can be added to food or drink. The form and property of the food or drink are not particularly limited so long as the effect of the active ingredient is not degraded, and the food or drink can be orally ingested, and it can be produced in a conventional manner by using raw materials usually used for food or drink except that the aforementioned active ingredient is added.

The amount of the compound or the composition of the present invention contained in the food or drink of the present invention is not particularly limited and can be suitably selected. For example, the compound or the composition of the present invention is contained in the food or drink in an amount of 0.0001 to 1% by mass, preferably 0.001 to 1% by mass, particularly preferably 0.005 to 1% by mass, in terms of the amount of the compound of the present invention.

The food or drink of the present invention can be used for various applications utilizing the pancreatic endocrine gland cell protecting effect or pancreatic endocrine gland cell function improving effect. For example, it can be used as food or drink suitable for "those who have low production of insulin", "those who have low function of insulin", "those who are getting concerned about their functions of pancreas", food or drink useful for decreasing or eliminating risk factors of lifestyle-related diseases such as diabetes mellitus caused by hypofunction of pancreas and pancreatitis caused by excessive ingestion of alcohol and stress.

As for the food or drink of the present invention, the expression "protection of pancreatic endocrine gland cells or improvement of pancreatic endocrine gland cell functions" means that improvement or prevention of various health damages resulted from hypofunction of pancreatic endocrine gland cells, and "protection of Langerhans islet functions", "improvement of Langerhans islet functions", "protection of β cell functions", "improvement of β cell functions", "enhancement of insulin production", "prevention of decrease of insulin production", "enhancement of insulin activity", "prevention of decrease of insulin activity" and so forth are exemplified in the present invention as terms having a meaning similar to that of the aforementioned "protection of pancreatic endocrine gland cells or improvement or pancreatic endocrine gland cell functions".

Furthermore, the food or drink of the present invention is useful for a prophylactic treatment of a disease resulted from hypofunction of pancreatic endocrine gland cells, for example, pancreatic function disorder in acute pancreatitis, chronic pancreatitis, type I diabetes mellitus, and type II diabetes mellitus, hypofunction of pancreas associating with senile decrease in insulin and so forth. Furthermore, the food or drink of the present invention can be used for a prophylactic treatment of various diseases, complications and so forth resulted from hypofunction of pancreatic endocrine gland cells, and can decrease risks of these diseases, complications and so forth. Furthermore, because the compound of the present invention exhibits low toxicity, the food or drink of the present invention is also useful for a patient administered with an antitumor agent in a treatment of pancreas cancer.

Examples of such various diseases and complications resulted from hypofunction of pancreatic endocrine gland cells include nerve disorder, nephropathy, retinopathy, cataract, macrovascular disease, diabetes and so forth.

The food or drink of the present invention is preferably marketed as food or drink attached with an indication that the food or drink is used for protection of pancreatic endocrine gland cells or improvement of pancreatic endocrine gland cell functions, for example, "food or drink containing a compound having a pancreatic endocrine gland cell protecting effect or a pancreatic endocrine gland cell function improving effect indicated as 'For protection of pancreatic endocrine gland cells or improvement of pancreatic endocrine gland cell functions'", "food or drink containing a plant extract indicated as 'For protection of pancreatic endocrine gland cells or improvement of pancreatic endocrine gland cell functions'", "food or drink containing *Aloe vera* extract indicated as 'For protection of pancreatic endocrine gland cells or improvement of pancreatic endocrine gland cell functions'" and so forth.

The wording used for such an indication as mentioned above is not necessarily be limited to the expression "For protection of pancreatic endocrine gland cells or improvement of pancreatic endocrine gland cell functions", and any other wording expressing the pancreatic endocrine gland cell protecting effect or pancreatic endocrine gland cell function improving effect of course falls within the scope of the present invention. As such a wording, for example, an indication based on various uses allowing consumers to recognize the pancreatic endocrine gland cell protecting effect or pancreatic endocrine gland cell function improving effect is also possible. Examples include indications of "Suitable for those who have low production of insulin", "Suitable for those who have low function of insulin", "Useful for decrease or elimination of risk factors (risks) of lifestyle-related diseases such as diabetes mellitus caused by reduction of insulin activity or production, pancreatitis caused by excessive ingestion of alcohol and stress" and so forth.

The aforementioned term "indication" includes all actions for informing consumers the aforementioned use, and any indications reminding or analogizing the aforementioned use fall within the scope of the "indication" of the present invention regardless of purpose, content, objective article, medium etc. of the indication. However, the indication is preferably made with an expression that allows consumers to directly recognize the aforementioned use. Specific examples include actions of indicating the aforementioned use on goods or packages of goods relating to the food or drink of the present invention, actions of assigning, delivering, displaying for the purpose of assigning or delivering or importing such goods or packages of goods indicated with the aforementioned use, displaying or distributing advertisements, price lists or business papers relating the goods with indicating the aforementioned use, or providing information including those as contents with indicating the aforementioned use by an electromagnetic method (Internet etc.) and so forth.

The indication is preferably an indication approved by the administration etc. (for example, an indication in a form based on an approval, which is qualified on the basis of any of various legal systems provided by the administration), and it is particularly preferably an indication on advertisement materials at the sales spots such as packages, containers, catalogs, pamphlets and POPs, others documents and so forth.

Examples of the indication further include indications as health food, functional food, enteric nutritive food, food for special dietary uses, food with nutrient function claims, quasi-drug and so forth as well as indications approved by the Ministry of Health, Labor and Welfare, for example, indications approved on the basis of the system of food for specified health uses and similar systems. Examples of the latter include indications as food for specified health uses, indications as food for specified health uses with qualified health claims, indications of influence on body structures and functions, indications of reduction of disease risk claims and so forth, and more precisely, typical examples include indications as food for specified health uses (especially indications of use for health) provided in the enforcement regulations of Health Promotion Law (Japan Ministry of Health, Labor and Welfare, Ministerial ordinance No. 86, Apr. 30, 2003) and similar indications.

EXAMPLES

The present invention will be explained more specifically with reference to the following examples. However, the scope of the present invention is not limited to the following examples.

Preparation Example 1

Examples of preparation of 3-O-β-D-glucopyranosyl-4-methyl-ergost-7-en-3-ol from Aloe vera will be described below.

3-O-β-D-Glucopyranosyl-4-methyl-ergost-7-en-3-ol was extracted from Aloe vera and purified as described below.

In an amount of 100 kg of mesophyll (clear gel portion) of Aloe vera was liquefied by using a homogenizer, added with 100 L of an ethyl acetate/butanol mixture (3:1) and stirred.

The mixture was left overnight to separate the ethyl acetate/butanol mixture and the aqueous layer, and the ethyl acetate/butanol mixture was recovered. The extract from this ethyl acetate/butanol mixture obtained by concentrating the ethyl acetate/butanol mixture under reduced pressure weighed 13.5 g.

Hyperglycemia improving effect was evaluated for the aforementioned aqueous layer and the extract from the ethyl acetate/butanol mixture in diabetes model mice described later in Reference Example 1, and the effect was observed for the extract from the ethyl acetate/butanol mixture. Therefore, it was attempted to isolate and purify components in the extract. First, the aforementioned extract was examined by thin layer chromatography (Merck Ltd., Silica gel 60F254 and RP-18F2543). As a result, an isolation method based on normal phase silica gel column chromatography using a chloroform/methanol mixture appeared to be suitable. Accordingly, a solution of 13 g of the aforementioned extract dissolved in 1 mL of a chloroform/methanol mixture (1:1) was loaded on a column filled with 400 g of silica gel 60 (Merck Ltd.) to attain adsorption of the components to the column, then the components were eluted with a chloroform/methanol mixture by the stepwise gradient method, in which the methanol concentration was increased stepwise (mixing ratios of chloroform:methanol=100:1, 25:1, 10:1, 5:1 and 1:1), and the eluate was fractionated for each mixing ratio of the aforementioned mixture. The yields of crude purification products obtained from the fractions after removing the solvent were 1.44, 3.0, 1.17, 1.28 and 2.27 g, respectively. It was confirmed by a method using the aforementioned model animals that, among these fractions, an active component existed in the fraction eluted with the mixture of chloroform:methanol=5:1 (crude purification product A). The existence of barbaloin or aloe-emodin was not confirmed by thin layer chromatography analysis.

Furthermore, to isolate and purify the active component from the aforementioned crude purification product A, this crude purification product A was examined by using thin layer chromatography (Merck Ltd., Silica gel 60F254 and RP-18F2543). As a result, an isolation method based on reverse phase silica gel column chromatography using methanol appeared to be suitable. Accordingly, the aforementioned crude purification product A was dissolved in 1 mL of a chloroform/methanol mixture (1:1) and loaded on a column filled with 180 g of COSMOSIL 140 (Nacalai Tesque, Inc.) to attain adsorption of the component to the column. Then, elution was performed by successively using 600 mL of 85% methanol solution, 600 mL of 95% methanol solution and 100 mL of 100% methanol. 3-O-β-D-Glucopyranosyl-4-methyl-ergost-7-en-3-ol was concentrated and isolated in a fraction eluted with 95% methanol and weighed 370 mg after removing the solvent. Hereafter, this product is referred to as compound 1.

Because the compound 1 showed an Rf value very close to that of β-sitosterol glucoside in an examination based on thin layer chromatography, it was anticipated to be a glycoside in which 1 molecule of sugar bound to the aglycon moiety. Furthermore, to examine the sugar composition of the compound 1, the compound 1 was subjected to methanolysis, then made into a TMS derivative and subjected to GC-MS measurement. As a result, in the measurement of the TMS derivative for the sugar portion of the compound 1, it showed main peaks at retention times of 14.28, 14.61 and 16.34 minutes, which were substantially consistent with the retention times of the main peaks of the sample glucose (Nacalai Tesque, Inc.), 14.27, 14.60 and 16.33 minutes. Furthermore, peaks corresponding to the main peaks of the sample galactose (Kishida Chemical Co., Ltd.) and the sample xylose (Kishida Chemical Co., Ltd.) were not observed. Thus, it was confirmed that the type of the sugar contained in the compound 1 was glucose.

From the above results, it was estimated that the compound 1 was a glycoside in which 1 molecule of glucose bound to the aglycon moiety. However, when the compound 1 was measured by $^{13}$C-NMR (125 MHz, CDCl$_3$), the existence of contaminants was confirmed. Therefore, it was considered that further purification should be required to determine its structure. Accordingly, the compound 1 was methanolyzed and then acetylated, and then the structure of the aglycon moiety as well as the binding site of the aglycon moiety and the sugar were confirmed. The method thereof will be described below.

Figure 2:
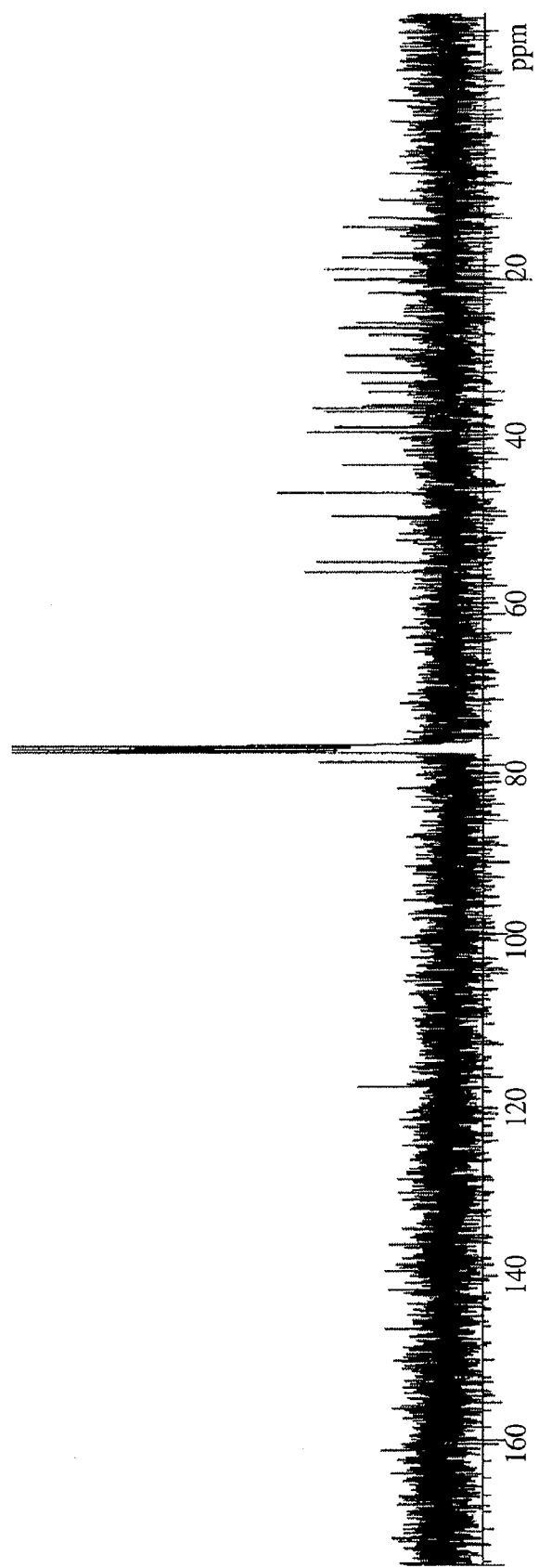
FIG. 2 shows a $^{13}$C-NMR chart of the acetylated aglycon moiety of the glycoside of the present invention (photo to replace drawing: a half-tone image shown on a display).

In an amount of 50 mg of the compound 1 was dissolved in methanol (50 mL) containing 5% hydrochloric acid, and the solution was refluxed with heating for 6 hours for methanolysis and dried to obtain a residue (about 30 mg). This residue was purified by silica gel column chromatography (hexane:chloroform=9:1) to obtain a compound 2 (10 mg). This compound 2 (5 mg) was added with acetic anhydride and pyridine (2 drops each) and heated at 70° C. for 30 minutes for acetylation, and then the solvent of the reaction mixture was evaporated to obtain a compound 3. The results of the analysis of this compound 3 by GC-MS and $^{13}$C-NMR (125 MHz, CDCl$_3$) are shown in FIGS. 1 and 2, respectively. The measurement conditions and results are as follows. 3-Acetoxy-4-methyl-ergost-7-ene used as a reference substance was prepared by extracting from aloe, purifying the extract, confirming the structure of the purified product by $^{13}$C-NMR and acetylating the same. [$^{13}$C-NMR spectrum (d values, in CDCl$_3$)]; C-1:36.8, C-2:27.3, C-3:78.7, C-4:37.0, C-5:46.9, C-6:26.8, C-7:117.4, C-8:139.4, C-9:49.7, C-10:34.9, C-11:21.6, C-12:39.7, C-13:43.6, C-14:55.1, C-15:23.1, C-16:28.2, C-17:56.3, C-18:12.0, C-19:14.2, C-20:36.5, C-21:19.0, C-22:33.9, C-23:30.6, C-24:39.1, C-25:32.6, C-26:20.4, C-27:18.4, C-28:15.6, C-29:15.3

[GC-MS]

Apparatus: GC-17A/GCMS5050A (SHIMADZU)
GC column: NEUTRA BOND-5 (GL Scienses)
Column temperature: 100° C. (2 min)→(10° C./min)→300° C. (28 min)
Injection temperature: 250° C.
Carrier gas: He (1.3 mL/min)
Interface temperature: 300° C.
MS mode: EI
Ionization energy: 70 eV

[Results]

Reference substance: 3-acetoxy-4-methyl-ergost-7-ene: tR [min]=39.4; m/z 456 [M]$^+$, 441 [M-CH$_3$]$^+$, 396 [M-AcOH]$^+$, 381 [M-CH$_3$—AcOH]$^+$
Compound 3: tR [min]=39.2; m/z 456 [M]$^+$, 441 [M-CH$_3$]$^+$, 396 [M-AcOH]$^+$, 381 [M-CH$_3$—AcOH]$^+$ The results of the NMR measurement of the compound 3 were consistent with the values of 3-acetoxy-4-methyl-ergost-7-ene shown in a literature (Yukagaku (Oil Chemistry), Vol. 36, No. 5, pp. 301-319, 1987). These results revealed that the compound 2 was 4-methyl-ergost-7-en-3-ol. Furthermore, as a result of FAB-MS measurement, the molecular weight of the compound 1 was found to be 576. When the compound 2 (aglycon moiety) and glucose were condensed, the molecular weight of the obtained compound was 414 (compound 2)+180 (glucose)−18 (water)=576, which was consistent with the molecular weight of the compound 1.

The above results revealed that the compound 1 had a structure of 3-O-β-D-glucopyranosyl-4-methyl-ergost-7-en-3-ol.

The molecular formulas, molecular weights and chemical formulas of the compounds are shown below.

(Compound 1)
Molecular formula: $C_{35}H_{60}O_6$
Molecular weight: 576
Chemical formula: The following chemical formula (1)

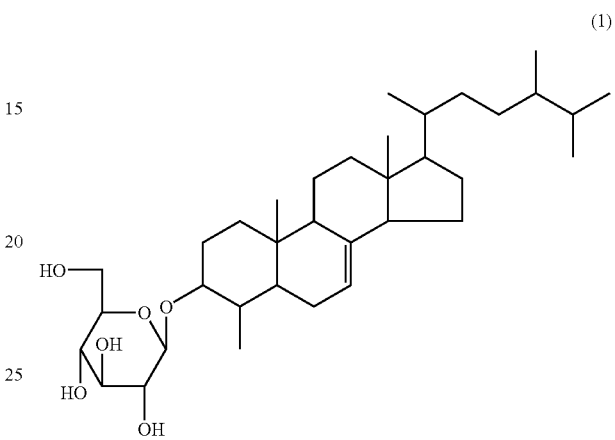

(1)

(Compound 2)
Molecular formula: $C_{29}H_{50}O$
Molecular weight: 414
Chemical formula: The following chemical formula (2)

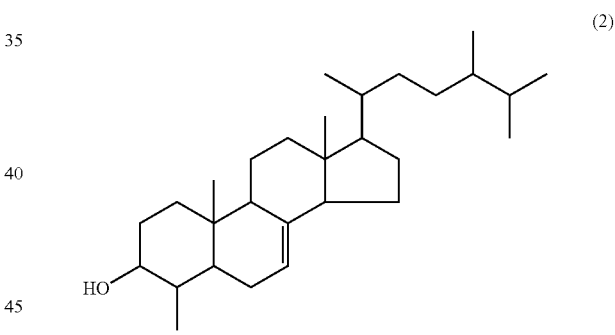

(2)

(Compound 3)
Molecular formula: $C_{31}H_{52}O_2$
Molecular weight: 456
Chemical formula: The following chemical formula (3)

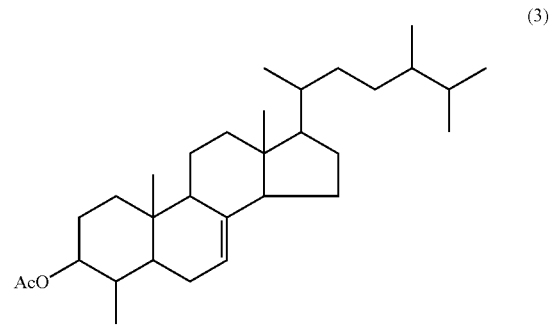

(3)

Preparation Example 2

Mesophyll (clear gel portion) of *Aloe vera* was dried by heating, 0.3 g of disrupted dry *Aloe vera* powder was added with 60 mL of 60, 80 or 100% ethanol, and the mixture was refluxed by heating at 60° C. for 1 hour. The extract was centrifuged at 1500 rpm for 20 minutes, and the supernatant was concentrated under reduced pressure to completely remove ethanol and thereby obtain a crude extract. The dry weights of the crude extracts obtained by extraction using 60, 80 and 100% ethanol were 65, 42 and 18 mg, respectively. It was confirmed by thin layer chromatography that these crude extracts contained 3-O-β-D-glucopyranosyl-4-methyl-ergost-7-en-3-ol.

Preparation Example 3

Mesophyll (clear gel portion) of *Aloe vera* was dried by heating, 0.3 g of disrupted dry *Aloe vera* powder was added with 60 mL of water, and the mixture was refluxed by heating at 95° C. for 5 hours. The extract was centrifuged at 1500 rpm for 20 minutes, and the supernatant was lyophilized to obtain 75 mg of a crude extract. It was confirmed by thin layer chromatography that this crude extract contained 3-O-β-D-glucopyranosyl-4-methyl-ergost-7-en-3-ol.

Preparation Example 4

Mesophyll (clear gel portion) of *Aloe vera* was dried by heating, disrupted and dried, 21 kg of *Aloe vera* powder thus prepared was added with 90 L of a chloroform/methanol: mixture (2:1), then immersed overnight in the mixture at room temperature and collected by filtration, and the residue obtained by the filtration was added with 90 L of chloroform/methanol mixture (2:1) again. This procedure was repeated 4 times in total. The obtained filtrate (350 L) was concentrated at 28° C. to finally obtain 784 g of a crude extract. In an amount of 780 g of this crude extract was added with 2 L of a chloroform/methanol mixture (2:1), stirred for 1 hour and filtered to recover the chloroform/methanol mixture layer (A). The residue obtained by the filtration was successively added with 2.5 L of water and 2 L of ethyl acetate and stirred for 1 hour, and the ethyl acetate layer (B) was recovered. The remaining aqueous layer was added with 5 L of chloroform again and stirred for 1 hour, and the chloroform layer (C) was recovered.

The recovered organic solvent extracts A, B and C were mixed, concentrated at 23° C. and loaded on a silica gel column [glass column: 52 mm×350 mm, packed material: IR-63/210-W (Daiso Co., Ltd.)]. Subsequently, while monitoring the eluate by thin layer chromatography, 10 L of a hexane/chloroform mixture (1:1), 10 L of chloroform, 20 L of a chloroform/methanol mixture (10:1) and 20 L of a chloroform/methanol mixture (5:1) were passed through the column in this order, and a fraction 1 (about 1 L), fraction 2 (about 1.5 L), fraction 3 (about 1.5 L) and fraction 4 (about 1.5 L) were recovered in the order of the used elution solvents.

It was confirmed by thin layer chromatography that, among these, the fraction 3 contained the objective glycoside, and then the solvent of the fraction 3 was removed to obtain 131.6 g of a crude extract. In an amount of 130 g of this crude extract was loaded on a silica gel column [glass column: 70 mm×500 mm, packed material: SP-60-40/60 (Daiso Co., Ltd.)] again and eluted successively with 10 L of a chloroform/methanol mixture (30:1), 50 L of a chloroform/methanol mixture (20:1), 10 L of a chloroform/methanol mixture (10:1) and 10 L of a chloroform/methanol mixture (1:1) as elution solvents under conditions of a pressure of 10 kgf·cm$^{-2}$ and a flow rate of 40 mL/min. The eluates were fractionated as 100-mL fractions by using a fraction collector to collect fractions 1 to 8.

The collected fractions were examined by thin layer chromatography, and as a result, it was revealed that the objective glycoside and contaminants existed in the fraction 7. Therefore, this fraction was concentrated, loaded on a silica gel column [glass column: 70 mm×500 mm, packed material: SP-60-40/60 (Daiso Co., Ltd.)] again, and successively eluted with 10 L of a chloroform/methanol mixture (20:1) and 10 L of a chloroform/methanol mixture (10:1) as elution solvents under conditions of a pressure of 10 kgf·cm$^{-2}$ and a flow rate of 40 mL/min. As a result, 25.3 g of 3-O-β-D-glucopyranosyl-4-methyl-ergost-7-en-3-ol was prepared, which was the objective glycoside contained in the fraction eluted with the chloroform/methanol mixture (10:1).

Reference Example 1

This test was performed in order to evaluate the hyperglycemic condition improving effect of 3-O-β-D-glucopyranosyl-4-methyl-ergost-7-en-3-ol.

(1) Preparation of Sample

The 3-O-β-D-glucopyranosyl-4-methyl-ergost-7-en-3-ol produced in Preparation Example 1 mentioned above was used as a test sample.

(2) Test Method

As type-II diabetes model mice, 6-week old male db/db mice (purchased from Clea Japan, Inc.) were used. These mice were divided into groups, each consisting of 7 animals. The test sample was dissolved in DMSO, and the concentration of 3-O-β-D-glucopyranosyl-4-methyl-ergost-7-en-3-ol was adjusted to 15 μg/mL with physiological saline. The final DMSO concentration was adjusted to 0.2%. The type-II diabetes model mice were orally administered with 1 mL of the test sample solution once a day everyday with a sonde. A solution that did not contain the test sample was used as a negative sample. Fasting blood glucose levels and random blood glucose levels were measured over time using Antisense II (Bayer-Sankyo Co., Ltd.). The fasting blood glucose levels were measured after 15 hours of fasting.

(3) Hyperglycemia Improving Effect

Figure 3:
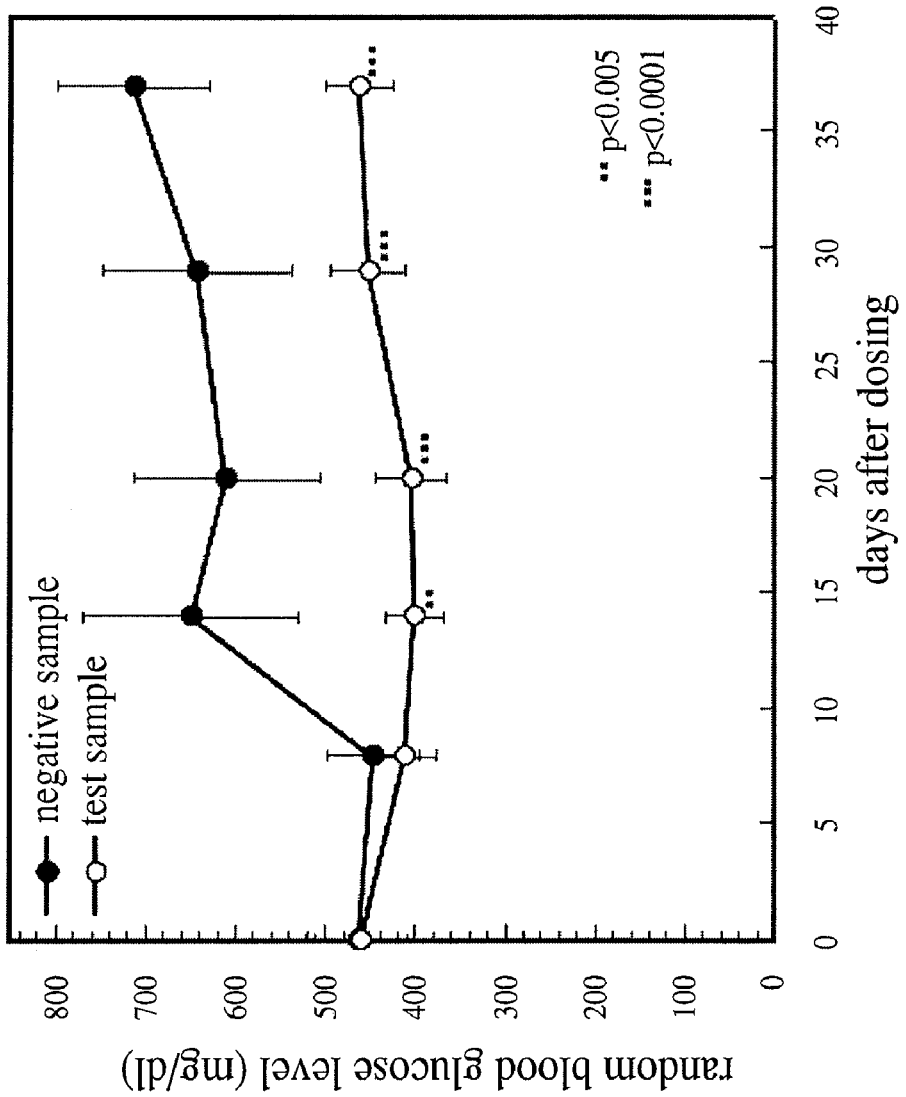
FIG. 3 shows a graph showing changes over time in random blood glucose levels of mice administered with the compound of the present invention.
Figure 4:
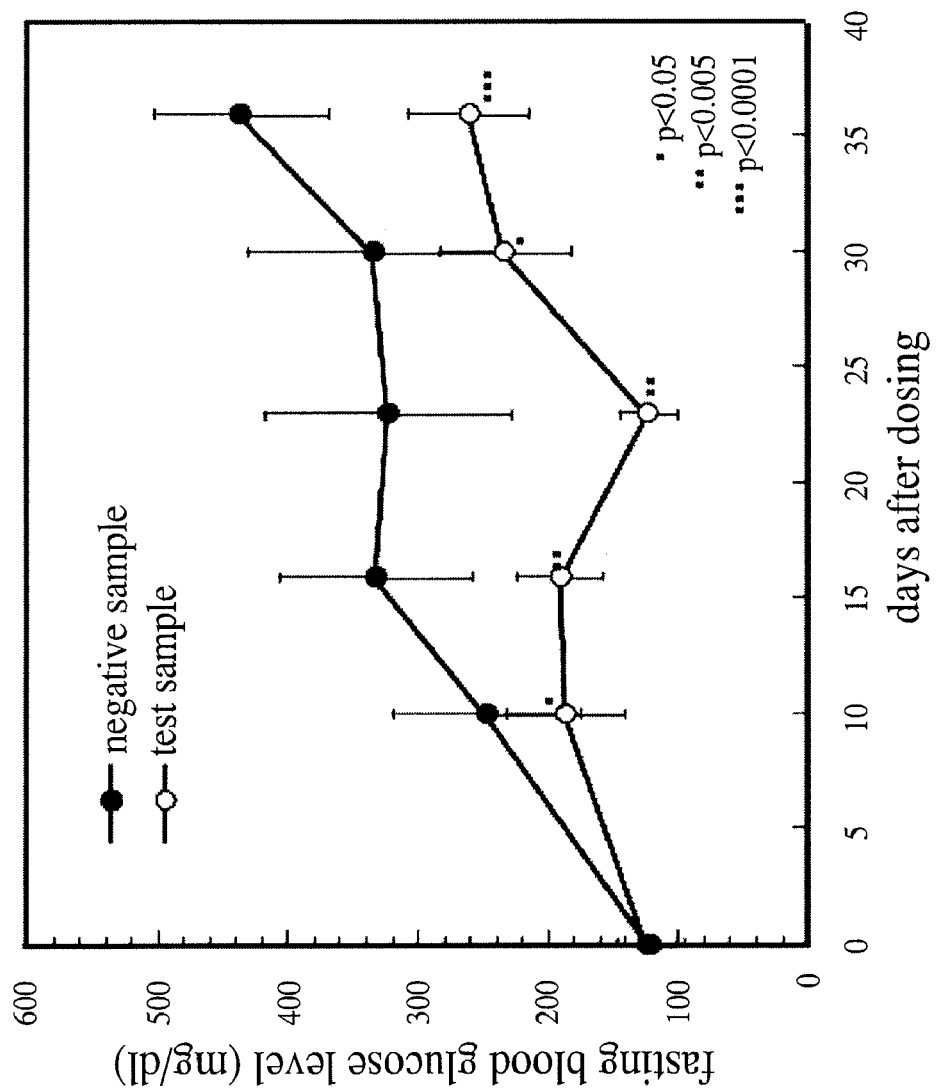
FIG. 4 shows a graph showing changes over time in fasting blood glucose levels of mice administered with the compound of the present invention.

Changes over time in random blood glucose levels and fasting blood glucose levels during the test sample administration period are shown in FIGS. 3 and 4. In the mice administered with the negative sample, rapid increase of glucose levels were observed in both the random blood glucose levels and fasting blood glucose levels, whereas effect of suppressing the increases in blood glucose levels was clearly observed in the mice repeatedly administered with the test sample.

Test Example 1

This test was performed in order to evaluate the pancreatic endocrine gland cell function (insulin production ability) protecting action of 3-O-β-D-glucopyranosyl-4-methyl-ergost-7-en-3-ol by using db/db mice known as a model animal of pancreatic hypofunction or pancreatic tissue dysfunction.

(1) Preparation of Sample

The 3-O-β-D-glucopyranosyl-4-methyl-ergost-7-en-3-ol produced in Preparation Example 1 mentioned above was used as a test sample.

(2) Test Method

In this test, 6-week old male db/db mice (purchased from Clea Japan, Inc.) were used. These mice were divided into groups, each consisting of 7 animals. Each test sample was dissolved in DMSO, and the concentration was adjusted to 0.1 or 1 μg/mL with physiological saline. The final DMSO concentration was adjusted to 0.2%. The model mice were orally administered with 1 mL of the test sample once a day everyday for 42 days with a sonde. The serum insulin level was measured on the 43rd day of the continuous administration by using Lbis insulin mouse ELISA kit (Shibayagi Co., Ltd).

(3) Test Results

The serum insulin levels on the 43rd day of the continuous administration of the samples are shown in Table 1. When the test sample 1 was administered at a concentration of 1 μg/animal, the serum insulin level was as high as 216% of that observed in the negative test, and thus pancreatic function (insulin production ability) protecting effect was clearly observed. On the other hand, when it was administered at a concentration of 0.1 μg/animal, any significant effect was not observed. During the administration period, no side-effect was observed at all in view of body weight and pathological findings.

TABLE 1

Serum insulin levels on 43rd day of continuous administration

| Sample | Serum insulin levels on $43^{rd}$ day of administration (ng/mL) | <p relative to negative sample> |
|---|---|---|
| Negative sample | 1.99 ± 0.66 | |
| Test sample (1 μg) | 4.29 ± 0.71 | <0.0001*> |
| Test sample (0.1 μg) | 2.24 ± 0.66 | <0.16> |

*indicates presence of statistically significant difference.

Test Example 2

In this test, the pancreatic tissue protecting action of 3-O-β-D-glucopyranosyl-4-methyl-ergost-7-en-3-ol was examined by using db/db mice known as a model animal of pancreatic hypofunction or pancreatic tissue dysfunction.

(1) Preparation of Sample

The 3-O-β-D-glucopyranosyl-4-methyl-ergost-7-en-3-ol produced in Preparation Example 1 mentioned above was used as a test sample.

(2) Test Method

In this test, 6-week old male db/db mice (purchased from Clea Japan, Inc.) were used. These mice were divided into groups, each consisting of 7 animals. Each test sample was dissolved in DMSO, and the concentration was adjusted to 1 μg/mL with physiological saline. The final DMSO concentration was adjusted to 0.2%. The model mice were orally administered with 1 mL of the test sample once a day everyday for 42 days with a sonde. On the 43rd day of the continuous administration, the pancreas was extracted, divided into three portions of upstream, midstream and downstream from the duodenum side, and fixed with a formalin solution, and then paraffin blocks were prepared in a conventional manner. Section slides were prepared from the paraffin blocks, and subjected to hematoxylin-eosin staining. The numbers of Langerhans islets existing on the sections of the 3 position of the pancreas, and area of Langerhans islet having the maximum area on each section were measured by using an ocular micrometer on a microscope ("ECLIPSE E600", NIKON CORP.).

(3) Test Results

The numbers of Langerhans islets in the pancreatic sections on the 43rd day of the continuous administration of the samples are shown in Table 2, and the maximum areas of Langerhans islets on the same day are shown in Table 3. The number of Langerhans islets of the mice administered with the test sample was 188% of the number of Langerhans islets of the negative sample-administered mice, and it was found that the number was clearly large. Similarly, the maximum areas of Langerhans islets in the mice administered with the test sample maintained 3.6 times as large as that observed in the negative test, and thus it was found that reduction of the Langerhans islets due to pancreatic dysfunction was prevented. From these results, it was revealed that 3-O-β-D-glucopyranosyl-4-methyl-ergost-7-en-3-ol had an action of protecting pancreatic tissues, especially endocrine gland cells.

TABLE 2

The numbers of Langerhans islets in pancreatic pathologic sections of treated mice

| Sample | The numbers of Langerhans islets in sections on $43^{rd}$ day of administration (piece) | <p relative to negative sample> |
|---|---|---|
| Negative sample | 40.3 ± 9.7 | |
| Test sample (1 μg) | 75.7 ± 24.7 | <0.04*> |

*indicates presence of statistically significant difference.

TABLE 3

Maximum areas of Langerhans islets in pancreatic pathologic sections of treated mice

| Sample | Maximum area of Langerhans islets on $43^{rd}$ day of administration × $10^3$ (μm$^2$) | <p relative to negative sample> |
|---|---|---|
| Negative sample | 44.5 ± 17.7 | |
| Test sample (1 μg) | 160.0 ± 116.7 | <0.04*> |

*indicates presence of statistically significant difference.

INDUSTRIAL APPLICABILITY

The drug and food or drink of the present invention can be safely administered or ingested and have an action of protecting pancreatic endocrine gland cells and improving the cell functions. Further, according to a preferred embodiment, the drug and food or drink of the present invention does not contain barbaloin or aloe-emodin, which are unfavorable components for a drug and food or drink.

What is claimed is:

1. A method for improving pancreatic functions, which comprises administering a purified compound having a structure represented by the following chemical compound or a composition containing the purified compound to a subject whose pancreatic functions are to be improved:

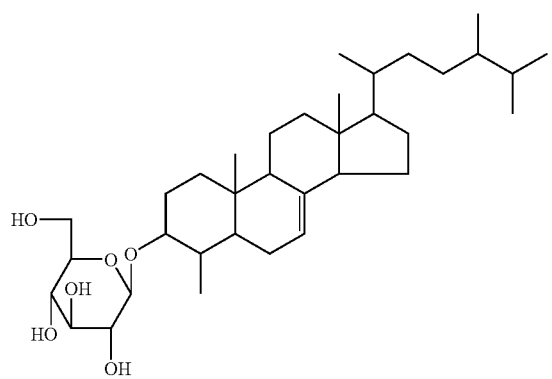

2. The method according to claim 1, wherein the improvement of pancreatic functions is to protect pancreatic endocrine gland cells or to improve pancreatic endocrine gland cell functions.

3. The method according to claim 1 or 2, wherein the purified compound is obtainable from an extract of a plant of the family Liliaceae or fraction thereof and wherein the composition contains 0.001% by dry mass or more of the purified compound.

* * * * *

UNITED STATES PATENT AND TRADEMARK OFFICE
CERTIFICATE OF CORRECTION

PATENT NO. : 7,531,520 B2
APPLICATION NO. : 11/576676
DATED : May 12, 2009
INVENTOR(S) : Tanaka et al.

It is certified that error appears in the above-identified patent and that said Letters Patent is hereby corrected as shown below:

Page 1, Column 2, Line 18, "Activity of *Aloa*" should be changed to --Activity of *Aloe*--

Page 1, Column 2, Line 30, "*Khimiya Prirodynykh*" should be changed to --*Khimiya Prirodnykh*--

Column 13, Line 41, "(GL Scienses)" should be changed to --(GL Sciences)--

Column 15, Line 31, "chloroform/methanol:" should be changed to --chloroform/methanol--

Signed and Sealed this

First Day of December, 2009

David J. Kappos
*Director of the United States Patent and Trademark Office*